United States Patent [19]

Matzke et al.

[11] Patent Number: 5,597,833
[45] Date of Patent: Jan. 28, 1997

[54] SUBSTITUTED QUINOL-2-YL-METHOXY-PHENYLACETIC ACID DERIVATIVES

[75] Inventors: Michael Matzke; Klaus-Helmut Mohrs, both of Wuppertal; Siegfried Raddatz; Romanis Fruchtmann, both of Cologne; Reiner Müller-Peddinghaus, Bergisch Gladbach; Armin Hatzelmann, Constance, all of Germany

[73] Assignee: Bayer Aktiengesellschaft, Leverkusen, Germany

[21] Appl. No.: 102,453

[22] Filed: Aug. 4, 1993

[30] Foreign Application Priority Data

Aug. 11, 1992 [DE] Germany .................. 42 26 519.3

[51] Int. Cl.$^6$ .................. C07D 215/14; A61K 31/47
[52] U.S. Cl. .................. 514/312; 514/311; 546/152; 546/153; 546/155; 546/170; 546/179; 546/180
[58] Field of Search .................. 546/152, 153, 546/155, 170, 179, 180; 514/311, 312

[56] References Cited

U.S. PATENT DOCUMENTS

| | | | |
|---|---|---|---|
| 4,929,626 | 5/1990 | Mohrs | 514/311 |
| 4,970,215 | 11/1990 | Mohrs et al. | 514/311 |
| 5,091,392 | 2/1992 | Raddatz | 514/311 |
| 5,126,354 | 6/1992 | Mohrs | 514/311 |
| 5,179,106 | 1/1993 | Mohrs | 514/311 |
| 5,192,771 | 3/1993 | Mohrs | 514/311 |
| 5,231,103 | 7/1993 | Matzke | 514/311 |
| 5,232,916 | 8/1993 | Zamboni | 514/311 |
| 5,304,563 | 4/1994 | Raddatz | 514/311 |
| 5,310,744 | 5/1994 | Raddatz | 514/314 |
| 5,358,955 | 10/1994 | Brooks | 514/311 |

FOREIGN PATENT DOCUMENTS

| | | |
|---|---|---|
| 0399416 | 11/1989 | European Pat. Off. . |
| 0344519 | 12/1989 | European Pat. Off. . |
| 0399291 | 11/1990 | European Pat. Off. . |
| 0414076 | 2/1991 | European Pat. Off. . |
| 0414078 | 2/1991 | European Pat. Off. . |
| 0545170 | 6/1993 | European Pat. Off. . |

OTHER PUBLICATIONS

P. Borgeat et al., "Arachidonic acid . . . A23187", Proc. Natl. Acad. Sci., USA 76 (1979), pp. 2148–2152.

*Primary Examiner*—C. Warren Ivy
*Assistant Examiner*—D. Margaret M. Mach
*Attorney, Agent, or Firm*—Sprung Horn Kramer & Woods

[57] ABSTRACT

Substituted quinol-2-yl-methoxy-phenylacetic acid derivatives are prepared by reacting correspondingly substituted phenols with quinolylmethyl halides or by reacting unsubstituted phenols with quinolylmethyl halides and subsequent alkylation. The substituted quinol-2-yl-methoxy-phenylacetic acid derivatives may be employed as active substances in medicaments.

4 Claims, No Drawings

SUBSTITUTED QUINOL-2-YL-METHOXY-PHENYLACETIC ACID DERIVATIVES

The present invention relates to substituted quinol-2-yl-methoxy-phenylacetic acid derivatives, processes for their preparation and their use in medicaments.

Substituted 4-(quinol-2-yl-methoxy)phenylacetic acid derivatives and α-substituted 4-(quinol-2-yl-methoxy)-phenylacetic acid derivatives are known from EP 344 519 (U.S. Pat. No. 4 970 215) and EP 339 416.

The present invention now relates to substituted quinol-2-yl-methoxy-phenylacetic acid derivatives of the general formula (I)

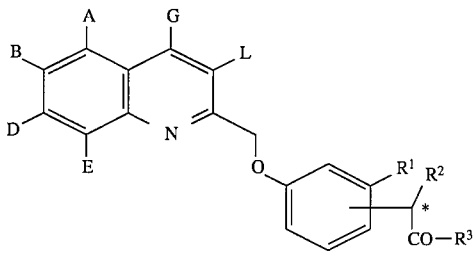

in which

A, B, D, E, G and L are identical or different and represent hydrogen, hydroxyl, halogen, cyano, carboxyl, nitro, trifluoromethyl, trifluoromethoxy or represent straight-chain or branched alkyl or alkoxy with in each case up to 8 carbon atoms, or represent aryl with 6 to 10 carbon atoms, which is optionally substituted by halogen, hydroxyl, nitro or cyano, $R^1$ represents halogen, cyano, nitro, azido, hydroxyl, carboxyl, trifluoromethyl, trifluoromethoxy or trifluoromethylthio, or represents straight-chain or branched alkyl, alkenyl or alkinyl with in each case up to 8 carbon atoms, which are optionally substituted by phenyl or cycloalkyl with 3 to 8 carbon atoms, or represents cycloalkyl with 3 to 8 carbon atoms or phenyl, or represents straight-chain or branched alkoxy or alkoxycarbonyl with in each case up to 6 carbon atoms, $R^2$ represents hydrogen or represents straight-chain or branched alkyl with up to 6 carbon atoms, or represents cycloalkyl with 3 to 12 carbon atoms, $R^3$ represents hydroxyl, or represents straight-chain or branched alkoxy with up to 8 carbon atoms or phenyl, or represents a group of the formula —$NR^4SO_2R^5$ or —$NR^6R^7$, in which $R^4$, $R^6$ and $R^7$ are identical or different and represent hydrogen, straight-chain or branched alkyl with up to 6 carbon atoms, phenyl or benzyl, $R^5$ represents trifluoromethyl or phenyl, which is optionally substituted by halogen, cyano, hydroxyl, nitro, trifluoromethyl, trifluoromethoxy or trifluoromethylthio, or by straight-chain or branched alkyl or alkoxy with in each case up to 6 carbon atoms, or represents straight-chain or branched alkyl with up to 8 carbon atoms, which is optionally substituted by phenyl, which in turn may be substituted by halogen, cyano, nitro, trifluoromethyl, trifluoromethoxy, trifluoromethylthio or hydroxyl or by straight-chain or branched alkyl or alkoxy with in each case up to 6 carbon atoms, and their salts.

Within the scope of the present invention, physiologically acceptable salts are preferred. Physiologically acceptable salts of the (quinol-2-ylmethoxy)-phenylacetic acid derivatives may be salts of the substances according to the invention with mineral acids, carboxylic acids or sulphonic acids. Particularly preferred salts are those, for example, with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts within the scope of the present invention are additionally salts of the monovalent metals, such as alkali metals, and the ammonium salts. Sodium, potassium and ammonium salts are preferred.

The compounds according to the-invention exist in stereoisomeric forms (*) which either do (enantiomers) or do not (diastereomers) relate to each other as image to mirror-image. The invention relates to both the antipodes and the racemic forms as well as to the diastereomeric mixtures. The racemic forms as well as the diastereomeric mixtures can be separated in a known manner into the stereoisomerically uniform components [cf. E. L. Eliel, Stereochemistry of Carbon Compounds, McGraw Hill, 1962].

Compounds of the general formula (I) are preferred, in which

A, B, D, E, G and L are identical or different and represent hydrogen, hydroxyl, fluorine, chlorine, bromine, carboxyl, nitro, trifluoromethyl or trifluoromethoxy or represent straight-chain or branched alkyl or alkoxy with in each case up to 6 carbon atoms, or represent phenyl, which is optionally substituted by fluorine, chlorine, bromine, hydroxyl, nitro or cyano, $R^1$ represents fluorine, chlorine, bromine, iodine, cyano, nitro, azido, hydroxyl, carboxyl, trifluoromethyl or trifluoromethoxy, or represents straight-chain or branched alkyl, alkenyl or alkinyl with in each case up to 6 carbon atoms, which are optionally substituted by phenyl, cyclopropyl, cyclopentyl or cyclohexyl, or represents cyclopropyl, cyclobutyl, cyclopentyl, cyclohexyl or cycloheptyl or phenyl, or represents straight-chain or branched alkoxy or alkoxycarbonyl with in each case up to 4 carbon atoms, $R^2$ represents hydrogen or represents straight-chain or branched alkyl with up to 4 carbon atoms, or represents cyclopropyl, cyclobutyl, cyclopentyl, cyclohexyl, cycloheptyl or cyclooctyl, $R^3$ represents hydroxyl, or represents straight-chain or branched alkoxy with up to 6 carbon atoms or phenyl, or represents a group of the formula —$NR^4SO_2R^5$ or —$NR^6R^7$, in which $R^4$, $R^6$ and $R^7$ are identical or different and represent hydrogen or straight-chain or branched alkyl with up to 4 carbon atoms, $R^5$ represents trifluoromethyl or phenyl, which is optionally substituted by fluorine, chlorine, bromine, iodine or cyano, or by straight-chain or branched alkyl or alkoxy with in each case up to 4 carbon atoms, or represents straight-chain or branched alkyl with up to 6 carbon atoms, which is optionally substituted by phenyl, which in turn may be substituted by fluorine, chlorine, bromine or trifluoromethyl or by straight-chain or branched alkyl or alkoxy with in each case up to 4 carbon atoms, and their salts.

Compounds of the general formula (I) are particularly preferred, in which
- A, B, D, E, G and L are identical or different and represent hydrogen, hydroxyl, fluorine, chlorine or bromine, or straight-chain or branched alkyl with up to 4 carbon atoms,
- $R^1$ represents fluorine, chlorine, bromine, nitro, azido or trifluoromethoxy, or represents straight-chain or branched alkyl, alkenyl or alkinyl with in each case up to 4 carbon atoms, which are optionally substituted by phenyl or cyclopropyl, or represents cyclopropyl, cyclopentyl or cyclohexyl,
- $R^2$ represents hydrogen, or represents straight-chain or branched alkyl with up to 3 carbon atoms, or represents cyclopentyl, cyclohexyl or cycloheptyl,
- $R^3$ represents hydroxyl, or represents straight-chain or branched alkoxy with up to 4 carbon atoms, or represents a group of the formula $-NR^4SO_2R^5$ or $-NR^6R^7$, in which
- $R^4$, $R^6$ and $R^7$, are identical or different and represent hydrogen or methyl,
- $R^5$ represents trifluoromethyl or phenyl, which is optionally substituted by fluorine, chlorine, bromine, iodine, methoxy, methyl or trifluoromethyl, or represents straight-chain or branched alkyl with up to 4 carbon atoms, which is optionally substituted by phenyl, which in turn may be substituted by fluorine, chlorine, bromine, methyl or methoxy, and their salts.

Compounds of the general formula (I) are very particularly preferred in which A, B, D, E, G and L represent hydrogen. Those compounds are also very particularly preferred in which the residue $-CHR^2-CO-R^3$ is located in the 4-position in relation to the quinolylmethoxy residue.

In addition, processes have been found for preparing the compounds according to the invention of the general formula (I), characterised in that

[A] phenols of the general formula (II)

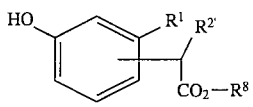

in which
- $R^1$ has the abovementioned meaning, $R^{2'}$ has the abovementioned meaning of $R^2$ but does not represent hydrogen, and
- $R^8$ represents $C_1-C_4$-alkyl, are etherified in inert solvents with 2-halogenomethylquinolines of the general formula (III)

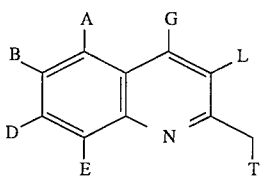

in which
- A, B, D, E, G and L have the abovementioned meaning and
- T represents halogen, preferably chlorine or bromine, or

[B] phenols of the general formula (IIa)

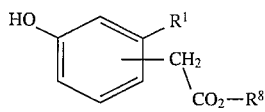

in which
- $R^1$ and $R^8$ have the abovementioned meaning, are first converted, by reaction with the compounds of the general formula (III) in inert solvents, into the compounds of the general formula (Ia)

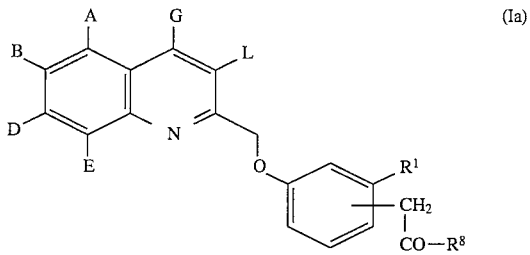

in which
- A, B, D, E, G, L, $R^1$ and $R^8$ have the abovementioned meaning, and the latter are subsequently alkylated in inert solvents with compounds of the general formula (IV)

$$R^{2'}-W \qquad (IV)$$

in which
- $R^{2'}$ has the abovementioned meaning and
- W represents chlorine, bromine or iodine, and in the case of the acids ($R^3=OH$) the esters are hydrolysed, and, in the case that $R^3$ represents the group of the formula $-NR^4SO_2R^5$ or $-NR^6R^7$, the acids ($R^3=OH$), optionally with prior activation, are sulphoamidated or amidated, respectively, with the corresponding sulphonamides of the formula (V) or the amines or ammonia of the formula (VI)

$$NHR^4SO_2-R^5 \qquad (V)$$

or $$HNR^6R^7 \qquad (VI)$$

in which
- $R^4$, $R^5$, $R^6$ and $R^7$ have the abovementioned meaning, and, in the case that $R^1$ represents alkenyl or alkinyl, reaction is carried out, starting from the corresponding halogeno compounds of the general formula (Ia/$R^1$=halogen, preferably bromine), with compounds of the general formula (VII)

$$(C_4H_9)_3Sn-R^{1'} \qquad (VII)$$

in which
- $R^{1'}$ represents $(C_1-C_8)$-alkenyl or alkinyl, in the presence of palladium(0) catalysts, preferably tetrakis(triphenylphosphine)palladium(0), and, in the case that $R^1=(C_1-C_8)$-alkyl, hydrogenation is optionally carried out subsequently according to customary methods, and, in the case of the enantiomers, the corresponding enantiomerically pure acids (I/$R^3$=OH) are separated by a customary method, and the substituents A, B, D, E, G, L and $R^1$ are optionally introduced or modified by further customary methods at each of the above-listed stages.
The processes according to the invention may be exemplified by the following formula diagrams:
[A]
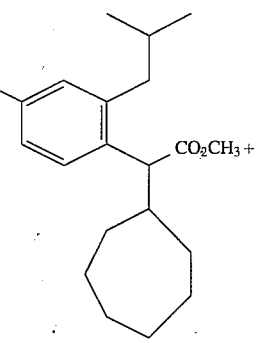
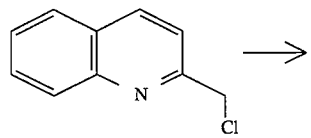
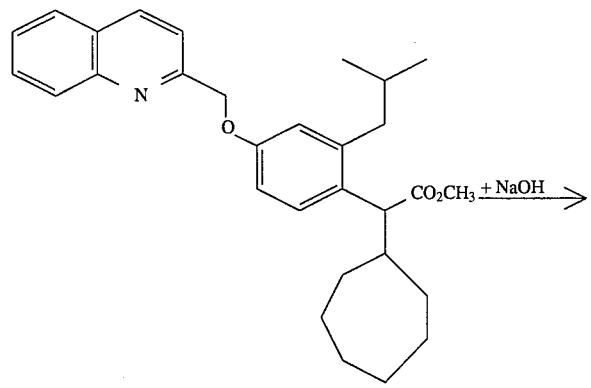
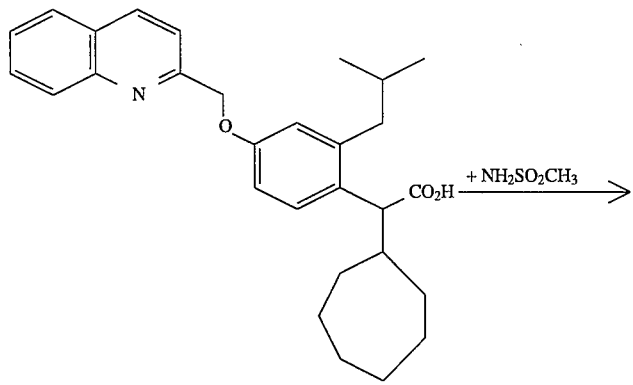

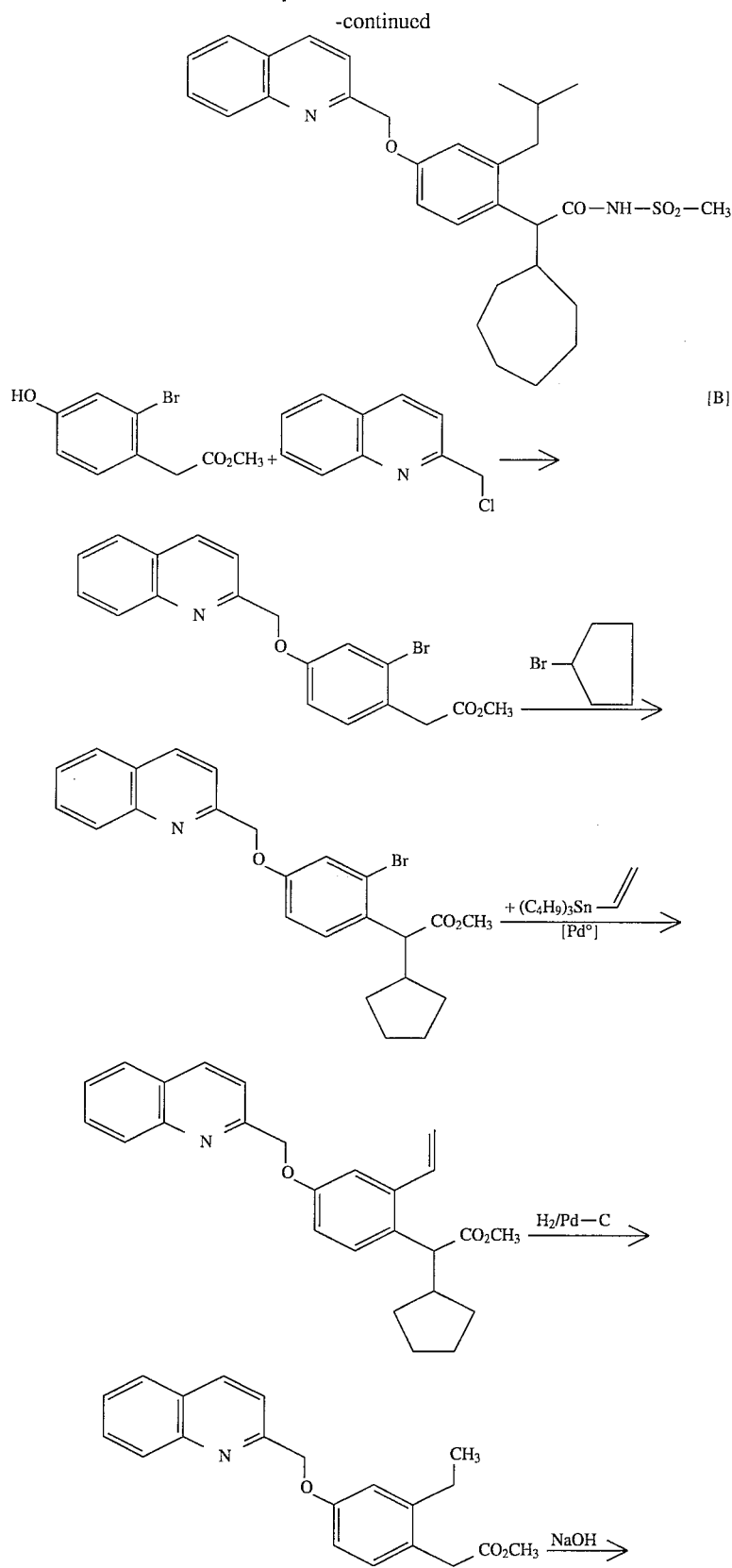

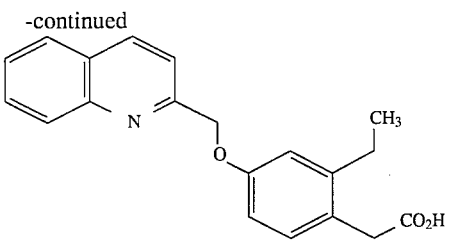

The etherification can be carried out in inert organic solvents, optionally in the presence of a base. Solvents for the etherification can be inert organic solvents which are not altered under the reaction conditions. Among these are, preferably, ethers such as, for example, dioxane, tetrahydrofuran or diethyl ether, halogenohydrocarbons such as dichloromethane, trichloromethane, tetrachloromethane, 1,2-dichloroethane or trichloroethylene, hydrocarbons such as benzene, xylene, toluene, hexane, cyclohexane or petroleum fractions, nitromethane, dimethylformamide, acetonitrile, acetone or hexamethylphosphoric acid triamide. It is also possible to employ mixtures of the solvents.

Inorganic or organic bases may be employed as bases for the etherification. Among these are, preferably, alkali metal hydroxides such as, for example, sodium hydroxide or potassium hydroxide, alkaline earth metal hydroxides such as, for example, barium hydroxide, alkali metal carbonates such as sodium Carbonate or potassium carbonate, alkaline earth metal carbonates such as calcium carbonate, or organic amines (trialkyl($C_1$–$C_6$)amines) such as triethylamine, or heterocycles such as pyridine, methylpiperidine, piperidine or morpholine.

It is also possible to employ, as bases, alkali metals, such as sodium, and their hydrides, such as sodium hydride.

The etherification generally takes place in a temperature range from 0° C. to +150° C., preferably from +10° C. to +100° C.

The etherification is generally carried out under atmospheric pressure. It is, however, also possible to carry out the process under reduced pressure or under elevated pressure (e.g. in a range from 0.5 to 5 bar).

In general, 0.5 to 5 mol, preferably 1 to 2 mol, of halide (III), based on 1 mol of the reaction partner, are employed. The base is generally employed in a quantity of 0.5 to 5 mol, preferably of 1 to 3 mol, based on the halide.

Suitable solvents for the alkylation are customary organic solvents which are not altered under the reaction conditions. Among these are, preferably, ethers such as diethyl ether, dioxane, tetrahydrofuran or glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoric acid triamide, acetonitrile, acetone or nitromethane. It is also possible to use mixtures of the said solvents. Dichloromethane is preferred.

The alkylation is carried out in the above-listed solvents at temperatures of 0° C. to +150° C., preferably at room temperature up to +100° C., and under atmospheric pressure.

The amidation and the sulphoamidation generally take place in inert solvents in the presence of a base and a dehydrating agent.

Suitable solvents in this context are inert organic solvents which are not altered under the reaction conditions. Among these are halogenohydrocarbons such as dichloromethane, trichloromethane, tetrachloromethane, 1,2-dichloroethane, trichloroethane, tetrachloroethane, 1,2-dichloroethane or trichloroethylene, hydrocarbons such as benzene, xylene, toluene, hexane, cyclohexane, or petroleum fractions, nitromethane, dimethylformamide, acetonitrile or hexamethylphosphoric acid triamide. It is also possible to employ mixtures of the solvents. Dichloromethane is particularly preferred.

Suitable bases for the amidation and the sulphoamidation are the customary basic compounds. Among these are, for example, alkali metal and alkaline earth metal hydroxides, such as lithium hydroxide, sodium hydroxide, potassium hydroxide or barium hydroxide, alkali metal hydrides such as sodium hydride, alkali metal or alkaline earth metal carbonates, such as sodium carbonate or potassium carbonate, or alkali metal alcoholates such as, for example, sodium methanolate or ethanolate, potassium methanolate or ethanolate or potassium tert-butylate, or organic amines such as benzyltrimethylammoniumhydroxide, tetrabutylammonium hydroxide, pyridine, triethylamine or N-methylpiperidine.

The amidation and the sulphoamidation are generally carried out in a temperature range from 0° C. to 150° C., preferably at 25° C. to 40° C.

The amidation and the sulphoamidation are generally carried out under atmospheric pressure. It is, however, also possible to carry out the process under reduced pressure or under elevated pressure (e.g. in a range from 0.5 to 5 bar).

In carrying out the amidation and the sulphoamidation, the base is generally employed in a quantity of 1 to mol, preferably of 1 to 1.5 mol, based on 1 mol of the particular carboxylic acid.

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride, or carbonyl compounds such as carbonyldiimidazole, or 1,2-oxazolium compounds such as 2-ethyl-5-phenyl-1,2-oxazolium3-sulphonate, or propanephosphonic anhydride or isobutyl chloroformate or benzotriazolyloxy-tris-(dimethylamino)phosphonium hexafluorophosphate or diphenylphosphoryl azide or methanesulphonyl chloride, optionally in the presence of bases such as triethylamine or N-ethylmorpholine or N-methylpiperidine or dicyclohexylcarbodiimide and N-hydroxysuccinimide.

It has, in particular, been found expedient to carry out the reaction in a stream of ammonia ($R^6R^7$=H) at slight excess pressure.

Hydrolysis of the carboxylic acid esters takes place according to customary methods by treating the esters in inert solvents with customary bases.

Suitable bases for the hydrolysis are the customary inorganic bases. Preferred among these are, for example, alkali metal hydroxides or alkaline earth metal hydroxides, such as, for example, sodium hydroxide, potassium hydroxide or barium hydroxide, or alkali metal carbonates such as sodium or potassium carbonate or sodium hydrogen carbonate. It is particularly preferred for sodium hydroxide or potassium hydroxide to be employed.

Suitable solvents for the hydrolysis are water or the organic solvents which are customary for a hydrolysis. Among these are, preferably, alcohols such as methanol, ethanol, propanol, isopropanol or butanol, or ethers, such as tetrahydrofuran or dioxane, or dimethylformamide or dimethyl sulphoxide. It is particularly preferred that alcohols such as methanol, ethanol, propanol or isopropanol are used. It is also possible to employ mixtures of the said solvents.

The hydrolysis is generally carried out in a temperature range from 0° C. to +100° C., preferably from +20° C. to +80° C.

In general, the hydrolysis is carried out under atmospheric pressure. It is, however, also possible to use reduced pressure or elevated pressure (e.g. from 0.5 to 5 bar).

In carrying out the hydrolysis, the base is generally employed in a quantity of 1 to 3 mol, preferably of 1 to 1.5 mol, based on 1 mol of the. ester. It is particularly preferred to use molar quantities of the reactants.

The hydrogenation generally takes place in inert solvents such as alcohols, such as, for example, methanol, ethanol, propanol or isopropanol, preferably in methanol, in the presence of a noble metal catalyst such as platinum, palladium, palladium on animal charcoal or Raney nickel, in a temperature range from 0° C. to +150° C., preferably from room temperature to +100° C., and under atmospheric pressure or under elevated pressure.

The pure enantiomers of the compounds according to the invention of the general formula (I) may be prepared, for example, by separating the corresponding acid racemates into the enantiomers according to a customary method and subsequently further reacting the enantiomers as indicated above.

The phenols of the general formulae (II) and (IIa) are known or, in particular in the case where $R^1$ represents alkyl, are, as concrete substance representatives, novel and may be prepared, for example, either by, in the case of the compounds of the general formula (IIa/$R^2$=H), initially carrying out a ring opening on compounds of the general formula (VIII)

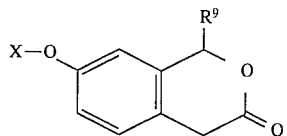

(VIII)

in which

X represents a hydroxyl-protective group such as, for example, benzyl or tert-butyl or else represents methyl, and $R^9$ represents straight-chain or branched alkyl with up to 7 carbon atoms, either by hydrogenation, preferably by reaction with hydrogen/Pd—C, and subsequently liberating the hydroxyl functionality by customary methods, for example with HBr, and in a final step esterifying with the corresponding alcohol, in the presence of an acid, preferably sulphuric acid, or by, in the case of the compounds of the general formula (II/$R^2$≠H), initially converting the compounds of the general formula (VIII), by alkylation with compounds of the abovementioned general formula (IV), into the compounds of the general formula (IX)

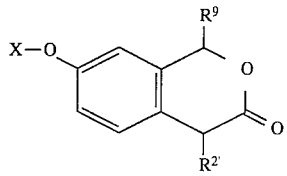

(IX)

in which

X, $R^{2'}$ and $R^9$ have the abovementioned meaning, and subsequently carrying out the ring opening, removal of the protective group and esterification as described above.

The alkylation and the hydrogenation take place under the conditions which have already been described above.

The reaction with hydrogen/Pd—C generally takes place in one of the solvents listed above, preferably methanol, in a temperature range from 0° C. to 70° C., preferably from 10° C. to 50° C., and under a pressure of 1 bar.

The esterification generally takes place with the corresponding alcohols in the presence of acids, preferably sulphuric acid, in a temperature range from 0° C. to 150° C., preferably from 50° C. to 100° C., and under atmospheric pressure.

The compounds of the general formula (VIII) are known in some cases or may be prepared according to known methods by, for example, starting from the protected 4-hydroxybenzyldialkylamines and carrying out a reaction of these with the corresponding aldehydes in the presence of bases, preferably butyllithium, in one of the abovementioned solvents, preferably diethyl ether, to give the corresponding substituted 2-hydroxymethylbenzyldialkyl compounds and subsequently cyclising with chloroformic acid ester, potassium cyanide and potassium hydroxide to the corresponding 1-substituted isochromanone compounds.

The compounds of the general formula (IX) are mostly novel and may be prepared, for example, according to the abovementioned process.

The removal of the protective groups from the corresponding ethers (VIII) and (IX) takes place according to a customary method, for example by hydrogenolytic cleavage of the benzyl ether in the abovementioned inert solvents in the presence of a catalyst with hydrogen gas.

The compounds of the general formula (III) are known or may be prepared according to known methods.

The compounds of the general formula (Ia) are novel and may be prepared as described above.

The compounds of the general formulae (IV), (V), (VI) and (VII) are known per se.

The compounds according to the invention can be employed as active substances in medicaments. The substances can act as inhibitors of enzymatic reactions within the scope of arachidonic acid metabolism, in particular of 5-lipoxygenase.

The compounds of the general formula (I) surprisingly demonstrate high in vitro activity as inhibitors of leukotriene synthesis, and a strong in vivo effect following oral administration.

They are consequently suitable, in a preferred manner, for the treatment and prevention of inflammations, in particular of disorders of the respiratory tract, such as allergies/asthma, bronchitis, emphysema, shock lung and pulmonary hypertension, inflammations/rheumatism and oedemas, thromboses and thrombo-embolisms, ischaemias (disturbances of peripheral, cardiac and cerebral blood flow), myocardial and cerebral infarcts, disturbances of cardiac rhythm, angina pectoris, arteriosclerosis, in tissue transplantations, dermatoses such as psoriasis, inflammatory dermatoses, e.g. eczema, dermatophyte infection, infections of the skin by bacteria, and metastases, and for cytoprotection in the gastrointestinal tract.

The compounds according to the invention can be employed both in human medicine and in veterinary medicine.

The data on the pharmacological activity of the substances according to the invention are determined by the following method:

As a measure of the inhibition of 5-lipoxygenase in vitro, the liberation of leukotriene $B_4$ ($LTB_4$) was determined in polymorphonuclear human leukocytes (PMN) following addition of substances and Ca ionophore by means of reverse-phase HPLC using the method of Borgeat, P. et al., Proc. Nat. Acad. Sci. 76, 2148–2152 (1979).

Pharmaceutical compositions which, besides inert, non-toxic, pharmaceutically suitable adjuvants and excipients, contain one or more compounds of the general formula (I), or which are composed of one or more active substances of the formula (I), as well as processes for preparing these compositions, also belong to the present invention.

The active substances of the formula (I) should be present in the compositions at a concentration of 0.1 to 99.5% by weight, preferably of 0.5 to 95% by weight, of the complete mixture.

Besides the active substances of the formula (I), the pharmaceutical compositions may also contain other pharmaceutical active substances.

The abovementioned pharmaceutical compositions may be prepared in a customary manner according to known methods, for example with the adjuvant (s) or excipient(s).

In general, it has been found advantageous, in order to achieve the desired result, to administer the active substance(s) of the formula (I) in total quantities of about 0.01 to about 100 mg/kg, preferably in total quantities of about 1 mg/kg to 50 mg/kg, of body weight every 24 hours, optionally in the form of several individual doses.

It can, however, where appropriate be advantageous to deviate from the said quantities, specifically depending on the nature and the body weight of the subject under treatment, on the individual response to the medicament, on the nature and severity of the disorder and on the nature of the formulation and its administration, as well as on the time or interval over which administration takes place.

Starting compounds

EXAMPLE I

Methyl 2-bromo-4-hydroxyphenylacetate

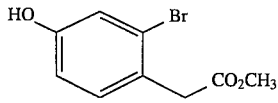

A solution of 70 g (0.303 mol) of 2-bromo-4-hydroxyphenylacetic acid in 560 ml of methanol and 14 ml of sulphuric acid is stirred at 80° C. for 3 h. Subsequently the mixture is concentrated in vacuo and the residue is taken up in dichloromethane. The organic phase is washed successively with water, saturated sodium hydrogen carbonate solution and water, dried over sodium sulphate and concentrated in vacuo. The crude product is purified by column chromatography (dichloromethane/methanol, 20:1)

Yield: 54.3 g (73.1% of theory)

EXAMPLE II

N-[2-(1-Hydroxyisobutyl)-4-methoxybenzyl]dimethylamine

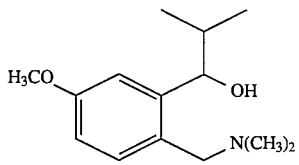

140 ml of a 1.6 molar solution of butyllithium in hexane (0.224 mol) are added dropwise at 0° C. and under an argon atmosphere to a mixture of 12.5 g (0.075 mol) of p-methoxybenzyldimethylamine in 60 ml of analytical grade diethyl ether. The mixture is stirred at room temperature for 24 h. Then 21.5 g (0.298 mol) of iso-butyraldehyde are added dropwise such that the reaction mixture boils under reflux. Subsequently the mixture is stirred at room temperature for 2 h and mixed with 150 ml of water, and the organic phase is extracted with half-concentrated hydrochloric acid. The product is extracted with ether from the aqueous phase following addition of 2N NaOH to pH 12. The organic phase is dried over sodium sulphate and concentrated in vacuo, and the residue is purified on silica gel 60 (dichloromethane/methanol, 9:1).

Yield: 13.7 g (77% of theory), oil.

EXAMPLE III

1-Isopropyl-7-methoxy-3-isochromanone

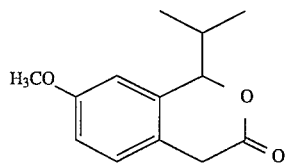

A solution of 148 ml (1.55 mol) of ethyl chloroformate in 200 ml of analytical grade toluene is added dropwise at room temperature to a mixture of 23.7 g (0.1 mol) of the compound from Example II and 60 g of sodium hydrogen carbonate in 375 ml of analytical grade toluene. The mixture is stirred at room temperature for 1 h. Subsequently it is filtered and the filtrate is concentrated in vacuo. The residue is mixed with 90 ml of analytical grade DMF and 20 g (0.3 mol) of potassium cyanide, and the reaction mixture is stirred at room temperature for 6 h. Subsequently water is added and extraction with ether is carried out, and the organic phase is dried over $Na_2SO_4$ and concentrated in vacuo. A mixture of the residue in 45 ml of methanol, 15 g of potassium hydroxide and 100 ml of water is heated under reflux for 8 h. After removal of the solvent by distillation in vacuo, water is added and the mixture is washed with ether. The aqueous phase is acidified with half-concentrated hydrochloric acid, and the product is extracted with ether. The organic phase is dried over sodium sulphate and concentrated in vacuo. The product is purified by column chromatography over silica gel 60 (petroleum ether/ether, 1:1).

Yield: 12.3 g (55.8% of theory), oil.

EXAMPLE IV

4-Cycloheptyl-1-isopropyl-7-methoxy-3-isochromanone

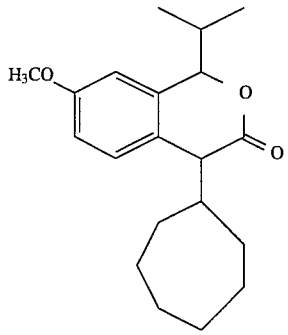

5.3 g (0.024 mol) of the compound from Example III and 8.5 g (0.048 mol) of cycloheptyl bromide are dissolved in 25 ml of analytical grade DMF. A solution of 5.9 g (0.053 mol) of potassium tert-butylate is added dropwise at 0° C. and under an argon atmosphere. The reaction mixture is stirred for 20 h and subsequently mixed with ice-water and acidified with half-concentrated hydrochloric acid to pH 5–6. The mixture is extracted with ethyl acetate and the organic phase is dried over sodium sulphate and concentrated in vacuo. The residue is chromatographed on silica gel 60 (petroleum ether/ether, 1:1)

Yield: 3.5 g (46% of theory), oil.

EXAMPLE V

2-Isobutyl-4-methoxyphenylacetic acid

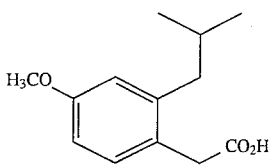

4.6 g (0.02 mol) of the compound from Example III are hydrogenated for 5 h at 1 bar in 200 ml of analytical grade methanol following addition of 1 g of Pd-carbon (10%). The catalyst is removed by filtration and the filtrate is concentrated in vacuo. The residue is taken up in ether and the organic phase is extracted with 3% strength sodium hydroxide. The alkaline aqueous phase is acidified with concentrated hydrochloric acid while cooling, and the product is extracted with ether. After drying over sodium sulphate, the organic product phase is concentrated in vacuo.

Yield: 2.8 g (64% of theory), oil.

EXAMPLE VI

2-Cycloheptyl-2-(2-isobutyl-4-methoxyphenyl)acetic acid

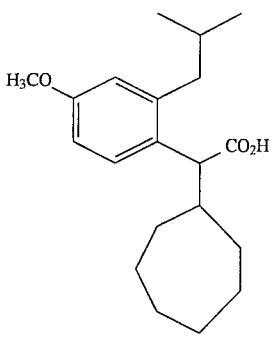

In analogy with the instructions for Example V, the title compound is prepared by hydrogenation of 4.3 g (0.014 mol) of the compound from Example IV in the presence of 1 g of palladium-carbon (10%).

Yield: 1.8 g (41.6% of theory) M.p.: 119° C.

EXAMPLE VII

4-Hydroxy-2-isobutylphenylacetic acid

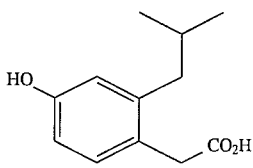

A mixture of 2.6 g (0.012 mol) of the compound from Example V and 50 ml of 8.8N (48% strength) hydrobromic acid is heated under reflux for 1 h. After cooling, the mixture is diluted with water and the product is extracted with ethyl acetate. The organic phase is dried over sodium sulphate and concentrated in vacuo. Yield: 2.4 g of crude product which is used directly for the next reaction.

EXAMPLE VIII

2-Cycloheptyl-2-(4-hydroxy-2-isobutylphenyl)acetic acid

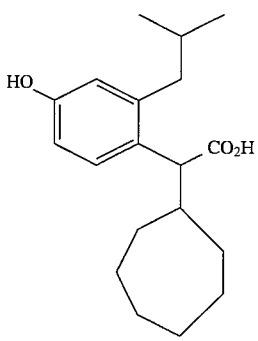

A mixture of 3.9 g (0.012 mol) of the compound from Example VI, 25 ml of 8.8N (48% strength) hydrobromic acid and 25 ml of glacial acetic acid is heated under reflux for 3 h. Subsequently the mixture is diluted with water and extracted with ethyl acetate. The organic phase is washed with water, dried over sodium sulphate and concentrated in vacuo. The product is purified by column chromatography on silica gel 60 (petroleum ether/ether 1:1)

Yield: 3.4 g (91.2% of theory), oil

EXAMPLE IX

Methyl 4-hydroxy-2-isobutylphenylacetate

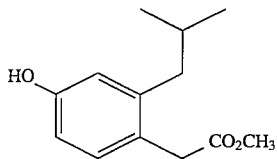

After addition of 30 ml of analytical grade methanol and 0.7 ml of conc. sulphuric acid, 2.4 g of the crude product of the compound from Example VII are heated under reflux for 3 h. After diluting with water and extracting with ethyl acetate, the organic phase is dried and concentrated in vacuo. The residue is chromatographed on silica gel 60 (dichloromethane/methanol, 50:1).

Yield: 1.7 g (65.4% of theory, based on the compound from Example V).

EXAMPLE X

Methyl 2-cycloheptyl-2-(4-hydroxy-2-isobutylphenyl)acetate

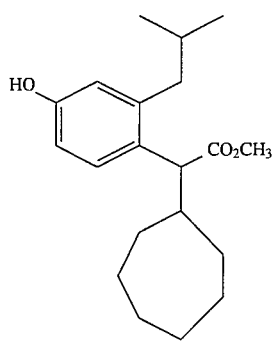

In analogy with the instructions for Example IX, the title compound is prepared from 2 g (7 mmol) of the compound from Example VIII.

Yield: 1.8 g (86% of theory), oil

PREPARATION EXAMPLES

Example 1

Methyl 2-bromo-4-(quinol-2-yl-methoxy)phenylacetate

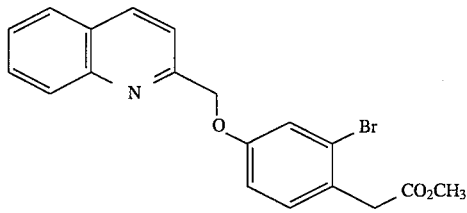

A mixture of 14.7 g (0.06 mol) of methyl 2-bromo-4-hydroxy-phenylacetate and 20.7 g (0.15 mol) of potassium carbonate in 150 ml of analytical grade DMF is stirred at 100° C. for 1.5 h. After adding 12.8 g (0.06 mol) of 2-chloromethylquinoline hydrochloride, the mixture is stirred at 100° C. for a further 8 h. Most of the solvent is subsequently distilled off in vacuo. The residue is taken up in ethyl acetate, and the organic phase is extracted with water, dried over sodium sulphate and concentrated in vacuo. The crude product is purified by column chromatography (dichloromethane/methanol, 50:1).

Yield: 14.8 g (63.9% of theory) M.p.: 90° C.

Example 2

Methyl 2-[2-bromo-4-(quinol-2-yl-methoxy)phenyl]-2-cyclopentyl-acetate

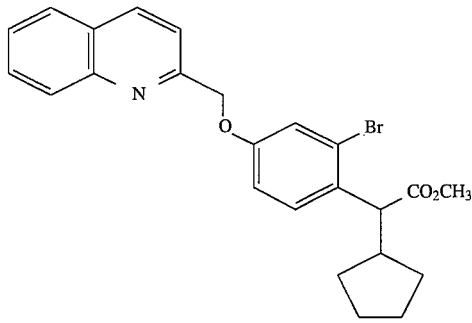

A solution of 3.77 g (0.034 mol) of potassium tertbutylate is added dropwise at 0° C. and under an argon atmosphere to a solution of 5.9 g (0.015 mol) of the compound from Example 1 and 4.6 g (0.031 mol) of cyclopentyl bromide in 20 ml of dimethylformamide. Subsequently, the mixture is stirred at room temperature for 10 h. The reaction mixture is poured into ice-water. Extraction with ethyl acetate is carried out, and the organic phase is dried over sodium sulphate and concentrated in vacuo. The residue is chromatographed over silica gel 60 (petroleum ether/ether, 1:1).

Yield: 5.6 g (80.6% of theory), oil

Example 3 and Example 4

Methyl 2-[2-allyl-4-(quinol-2-yl-methoxy)phenyl]-2-cyclopentylacetate (Example 3)

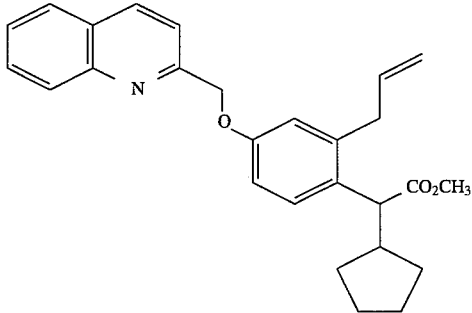

Methyl 2-[4-(quinol-2-yl-methoxy)-2-cyclopropylphenyl]-2-cyclopentylacetate (Example 4)

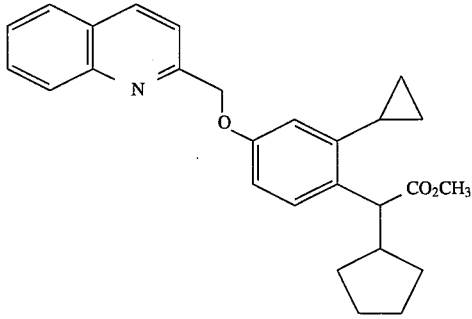

A reaction mixture of 16 g (0.035 mol) of methyl 2-[2-bromo-4-(quinol-2-yl-methoxy)phenyl]-2-cyclopentylacetate, 13.2 g (0.039 mol) of allyltributyltin and 1.6 g (1.4 mmol) of tetrakis(triphenylphosphine)palladium(0) in 160 ml of analytical grade toluene is stirred at 120° C. under argon and with the exclusion of light for 19 h. Subsequently, the solid is filtered off and the filtrate is concentrated in vacuo. The product mixture is purified by column chromatography (petroleumether/ether 1:1); the products are not separated at this stage.

Yield: 11.1 g ((3) allyl/(4) cyclopropyl, 7:3) (73.5% of theory)

Example 5

Methyl 2-allyl-4-(quinol-2-yl-methoxy)phenylacetate

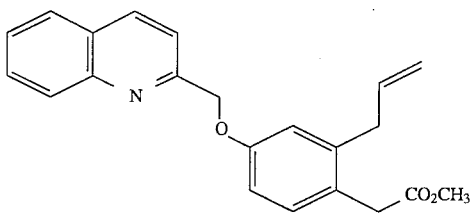

In analogy with the instructions in Example 3, the title compound is prepared from 15.2 g (0.040 mol) of the compound from Example 1 and 14.4 g (0.044 mol) of allyltributyltin in the presence of 1.8 g (1.6 mmol) of tetrakis(triphenylphosphine)-palladium(0).

Yield: 8.7 g (62.5% of theory), oil

Example 6 and Example 4

Methyl 2-[4-(quinol-2-yl-methoxy)-2-propylphenyl]-2-cyclopentylacetate (Example 6)

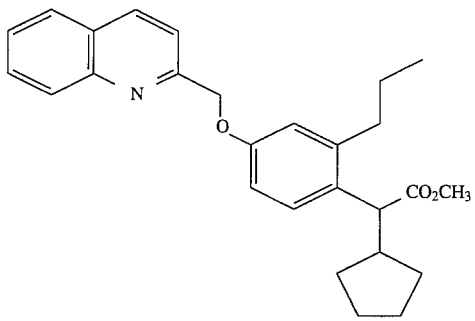

Methyl 2-[4-(quinol-2-yl-methoxy)-2-cyclopropylphenyl]-2-cyclopentylacetate (Example 4)

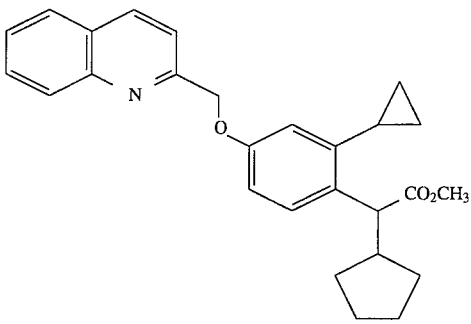

1.1 g of the product mixture from Examples 3 and 4 are dissolved in 190 ml of methanol and hydrogenated in the presence of 1.5 g of palladium/carbon (10%) for 4 h under 1.5 bar. The catalyst is filtered off, the filtrate is concentrated in vacuo and the product mixture is chromatographed on silica gel 60 (petroleum ether/ethyl acetate, 10:1).

Yield: 5.9 g (Example 6)
Yield: 2.5 g (Example 4)

Example 7

Methyl 4-(quinol-2-yl-methoxy)-2-propyl-phenylacetate

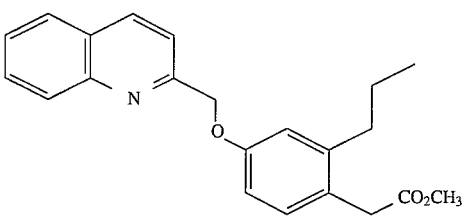

8.7 g (0,025 mol) of .the compound from Example 5 are hydrogenated in analogy with the instructions in Examples 6 and 4 in the presence of 1.3 g of palladium/carbon (10%).

Yield: 3.6 g (42.3% of theory), oil

Example 8

Methyl 2-[2-bromo-4-(quinol-2-yl-methoxy)phenyl]2-cycloheptylacetate

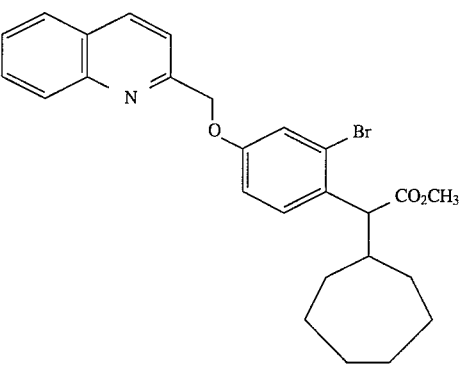

In analogy with the instructions in Example 2, the title compound is prepared from 23.6 g (0.061 mol) of the compound from Example 1, 21.6 g (0.122 mol) of cycloheptyl bromide and 15 g (0,122 mol) of potassium tertbutylate.

Yield: 16.4 g (55.6% of theory)

Example 9

Methyl 2-[4-(quinol-2-yl-methoxy)-2-vinylphenyl]-2-cyclopentylacetate

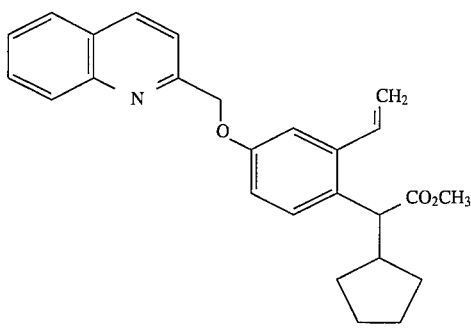

A mixture of 2.3 g (5 mmol) of the compound from Example 2, 1.6 g (5 mmol) of tributylvinyltin and 223 mg (0.2 mmol) of tetrakis(triphenylphosphine)palladium(0) in 40 ml of analytical grade toluene is heated under reflux for 15 h under an argon atmosphere and with exclusion of light. Subsequently, the solid is filtered off and the filtrate is concentrated in vacuo. Purification by column chromatography on silica gel 60 with petroleum ether/ether (1:1) follows. The resulting product is contaminated with tin salts and is used directly for further reaction.

Yield: 2.5 g of crude product, oil

Example 10

Methyl 2-[4-(quinol-2-yl-methoxy)-2-ethylphenyl]-2-cyclopentylacetate

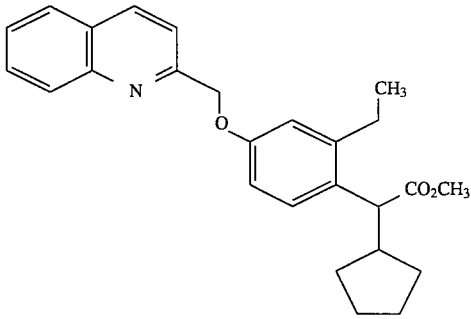

4 g (0.01 mol) of the compound from Example 9 are dissolved in 10 ml of dichloromethane p.a. and 70 ml of analytical grade methanol and hydrogenated for 6 h under 2 bar in the presence of 800 mg of Pd-carbon (10%). The catalyst is filtered off and the filtrate is concentrated to 70 ml volume and hydrogenated once more for 4 h under bar in the presence of 800 mg of Pd-carbon (10%). After filtration to remove the catalyst, the mixture is concentrated in vacuo and the residue is chromatographed on silica gel 60.

Yield: 1.1 g (27.4% of theory), oil

Example 11

Methyl 2-[4-(quinol-2-yl-methoxy)-2-vinylphenyl]-2-cycloheptylacetate

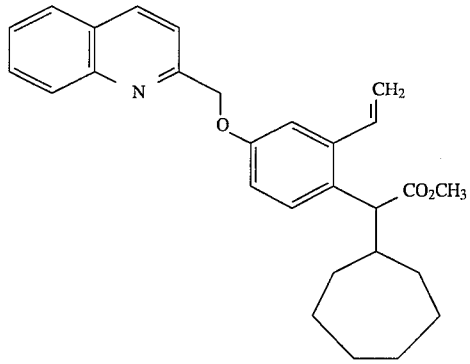

In analogy with the instructions in Example 9, the title compound is prepared from 7.2 g (0.015 mol) of the compound from Example 8 and 4.8 g (0.015 mol) of tributylvinyltin in the presence of 670 mg (0.006 mol) of tetrakis(triphenylphosphine)-palladium(0).

Yield: 6.8 g of crude product (contaminated with tin salts). The crude product is directly used for further reaction.

Example 12

Methyl 2-[4-(quinol-2-yl-methoxy)-2-phenylethinylphenyl]-2-cyclopentylacetate

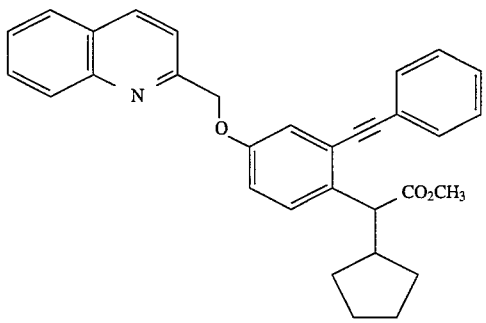

A mixture of 9.8 g (0.022 mol) of the compound from Example 2, 20 g (0.054 mol) of phenylethinyltributyltin and 2.3 g (2 mmol) of tetrakis(triphenylphosphine)palladium(0) in 80 ml of analytical grade toluene is heated under reflux for 36 h under an argon atmosphere and with exclusion of light. The mixture is concentrated in vacuo and the residue is purified by column chromatography (petroleum ether/ether, 1:1).

Yield: 9.0 g (87.7% of theory), oil

Example 13

Methyl 4-(quinol-2-yl-methoxy)-2-isobutylphenylacetate

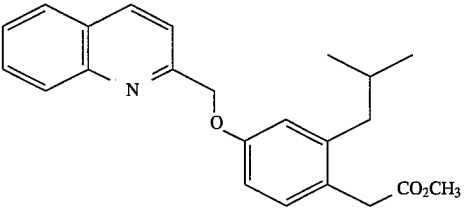

In analogy with the instructions in Example 1, the title compound is prepared from 1.7 g (7.7 mmol) of methyl 4-hydroxy-2-isobutylphenylacetate, 2.64 g (0.019 mol) of potassium carbonate and 1.63 g (7.7 mmol) of 2-chloromethylquinoline hydrochloride.

Yield: 2.17 g (78% of theory), oil

Example 14

Methyl 2-[4-(quinol-2-yl-methoxy)-2-isobutylphenyl]-2-cycloheptylacetate

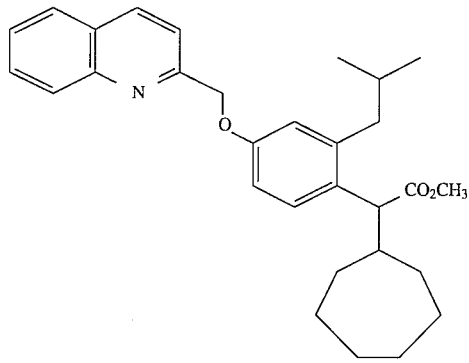

In analogy with the instructions in Example 1, the title compound is prepared from 1.59 g (5mmol) of methyl 2-(4-hydroxy-2-isobutylphenyl)-2-cycloheptylacetate, 1.66 g (12 mmol) of potassium carbonate and 1.07 g (5 mmol) of 2-chloromethylquinoline hydrochloride.

Yield: 2 g (89% of theory), oil

Example 15

2-[2-Bromo-4-(quinol-2-yl-methoxy)phenyl]-2-cyclopentylacetic acid

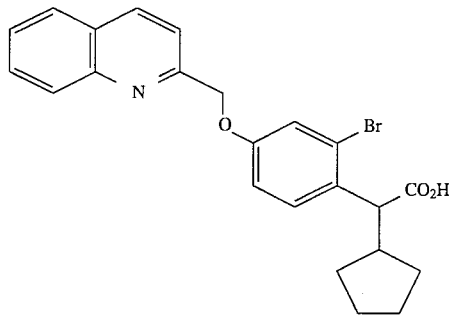

50 ml of methanol and 8 ml of 1N NaOH are added to 2.2 g (4.8 mmol) of the compound from Example 2. The reaction mixture is heated under reflux for 20 h and subsequently concentrated in vacuo and the residue is taken up in water/diethyl ether and washed with diethyl ether. The aqueous phase is acidified with 2N hydrochloric acid and extracted with diethyl ether. After evaporating the solvent in vacuo, the crude product is chromatographed on silica gel 60 (dichloromethane/methanol, 9:1).

Yield: 1.85 g (86.8% of theory) M.p.: 73°–75 °C.

Example 16

2-[4-(Quinol-2-yl-methoxy)-2-isobutylphenyl]-2-cycloheptylacetic acid

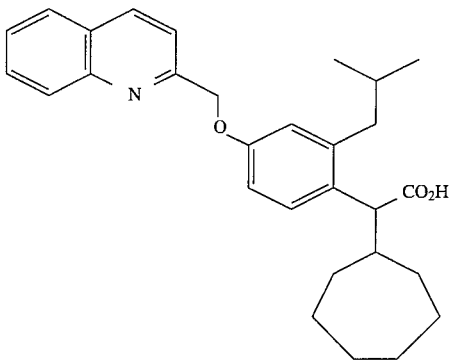

A mixture of 2 g (4.3 mmol) of the compound from Example 14, 12 ml of isopropanol and 12 ml of 1N NaOH is heated under reflux for 12 h. Subsequently, the mixture is concentrated in vacuo, water and diethyl ether are added and this mixture is extracted with diethyl ether. The organic phase is concentrated in vacuo and the recovered starting compound is hydrolysed once again. The combined aqueous phases are acidified with 2N hydrochloric acid and extracted with ethyl acetate. The organic phase is dried over sodium sulphate and concentrated in vacuo. The crude product is recrystallised in methanol. 3 reaction cycles are carried out to achieve complete hydrolysis.

Yield: 1.45 g (76.7% of theory) M.p.: 178°–180° C.

The compounds listed in Table 1 are prepared in analogy with the instructions in Examples 15 and 16.

TABLE 1

| Ex. No. | $R^1$ | $R^2$ | M.p. (°C.) (solvent) | Yield (% of theory) |
|---|---|---|---|---|
| 17 | isobutyl | H | 176–178 (CH₃OH) | 83.5 |
| 18 | isobutyl | cyclopentyl | 129–131 (CH₂Cl₂) | 73.1 |
| 19 | isopropyl | H | 138–140 (CH₃OH) | 73 |
| 20 | cyclopropyl | cyclopentyl | 152–153 (diethyl ether) | 37 |

TABLE 1-continued

[Structure: quinoline-CH2-O-phenyl(R1)-CH(R2)-CO2H]

| Ex. No. | R¹ | R² | M.p. (°C.) (solvent) | Yield (% of theory) |
|---|---|---|---|---|
| 21 | allyl | cyclopentyl | 129–131 (ethyl acetate) | 86.2 |
| 22 | allyl | cycloheptyl | 145–147 (diethyl ether) | 67.2 |
| 23 | propyl | cyclopentyl | 115–117 (ethyl acetate) | 25.8 |
| 24 | phenylethynyl | cyclopentyl | 215–217 (ethyl acetate) | 78 |

Example 25

N-{2-[2-Bromo-4-(quinol-2-yl-methoxy)phenyl]-2-cyclopentylacetyl}-methanesulphonamide

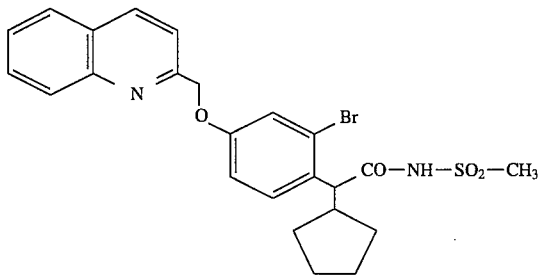

A solution of 1.2 g (2.64 mmol) of the compound from Example 15, 280 mg (2.9 mmol) of methanesulphonamide, 0.76 g (3.96 mmol) of N-(3-dimethylamino-propyl)-N'-ethylcarbodiimide hydrochloride and 0.35 g (2.9 mmol) of 4-dimethylaminopyridine in 60 ml of analytical grade dichloromethane is stirred at room temperature for 20 h. Subsequently, the organic phase is washed with water, dried over sodium sulphate and concentrated in vacuo. The residue is purified by column chromatography on silica gel 60 (dichloromethane/methanol, 50:1).

Yield: 0.9 g (65.9% of theory), oil

Example 26

N-{2-[4-(quinol-2-yl-methoxy)-2-propylphenyl]acetyl}-N-methyl-trifluoromethanesulphonamide

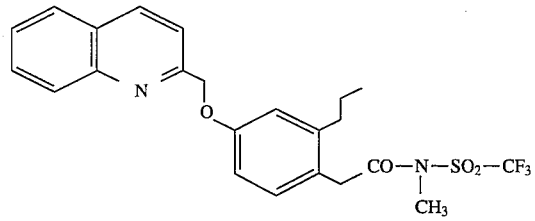

0.37 ml (4.8 mmol) of methanesulphonyl chloride are added dropwise at 0° C. to a suspension of 0.67 g (2 mmol) of 2-[4-(quinol-2-yl-methoxy)-2-propylphenyl]acetic acid and 0.55 ml (4 mmol) of triethylamine in 20 ml of analytical grade tetrahydrofuran. After 15 min, a solution of 0.59 g (3.6 mmol) of N-methyltrifluoromethanesulphonamide and 0.49 g (4 mmol) of 4-dimethylaminopyridine in 5 ml of analytical grade tetrahydrofuran is added dropwise at 0° C. The reaction mixture is stirred at room temperature for 20 h and subsequently poured into ice-water and extracted with ethyl acetate. The organic phase is dried over sodium sulphate and concentrated in vacuo. Purification of the residue by column chromatography on silica gel 60 (dichloromethane/methanol, 20:1) follows.

Yield: 0.73 g (76% of theory) M.p.: 111°–112° C.

The compounds listed in Table 2 are prepared in analogy with the instructions in Examples 25 and 26.

TABLE 2
| Ex. No. | R¹ | R² | R³ | M.p. (°C.) (solvent) | Yield (% of theory) |
|---|---|---|---|---|---|
| 27 | Br |  | —NHSO$_2$—CH$_2$C$_6$H$_5$ | 72–74 (CH$_2$Cl$_2$) | 70.2 |
| 28 | Br |  | —NHSO$_2$—C$_6$H$_4$-p-CH$_3$ | oil | 38.3 |
| 29 |  | H | —NHSO$_2$CH$_3$ | 155–157 (CH$_2$Cl$_2$) | 89.5 |
| 30 |  |  | —NHSO$_2$CH$_3$ | 133–134 (diethyl ether) | 62.4 |
| 31 |  | H | —NHSO$_2$CH$_3$ | 130–132 (CH$_2$Cl$_2$) | 40.4 |
| 32 |  | H | —N(CH$_3$)SO$_2$CF$_3$ | 93–95 (CH$_2$Cl$_2$) | 62.7 |
| 33 | 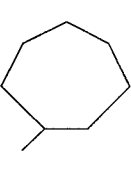 |  | —NHSO$_2$CH$_3$ | 97–99 (CH$_2$Cl$_2$) | 55.4 |
| 34 |  |  | —NHSO$_2$CH$_3$ | 88–90 (diethyl ether) | 44.1 |
| 35 |  | 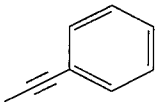 | —NHSO$_2$CH$_3$ | amorphous | 48.8 |
| 36 |  | | —NHSO$_2$CH$_3$ | 110–120 (CH$_2$Cl$_2$) | 89.9 |

TABLE 2-continued
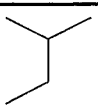
| Ex. No. | R¹ | R² | R³ | M.p. (°C.) (solvent) | Yield (% of theory) |
|---|---|---|---|---|---|
| 37 | 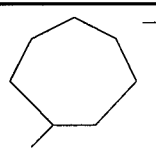 | 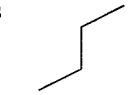 | —NH$_2$ | 119–121 (diethyl ether) | 38.7 |
| 38 |  | 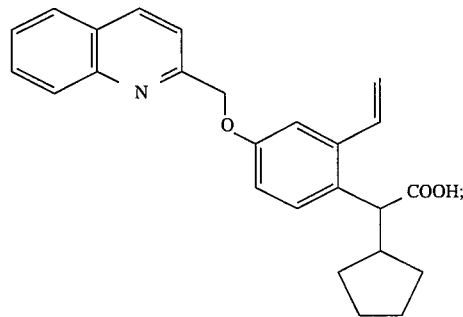 | —NH$_2$ | 109–111 (CH$_2$Cl$_2$) | 63.1 |
We claim:
1. A compound selected from the group consisting of compounds of the formula:
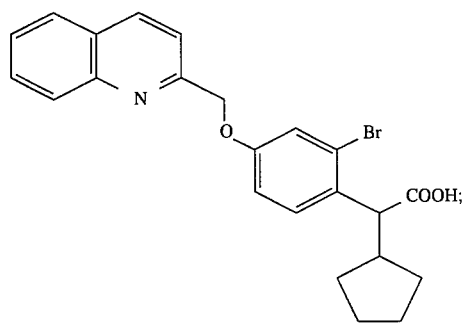
and
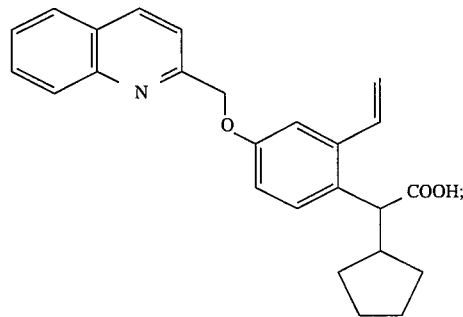
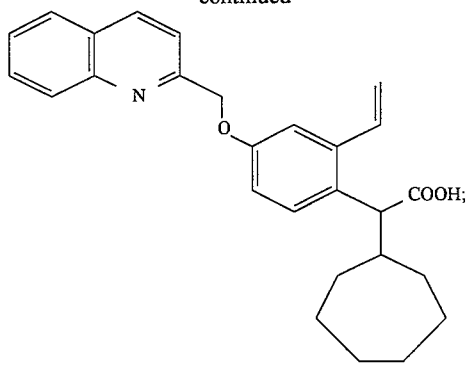
or a pharmaceutically acceptable salt thereof.
2. A compound according to claim 1 wherein such compound is 2-[4-(Quninolin-2-yl-methoxy)-2-allylphenyl]-2-cycloheptyl acetic acid of the formula
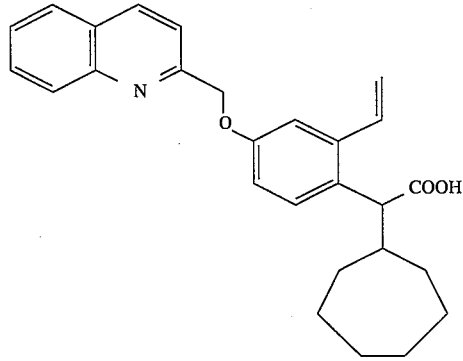

or a pharmaceutically acceptable salt thereof.

3. A composition for inhibiting the leukotriene synthesis comprising an amount effective therefore of a compound or salt thereof according to claim 1 and a pharmacologically acceptable diluent.

4. A method of inhibiting the synthesis of leukotriene synthesis in a patient in need thereof which comprises adminitering to such patient an amount effective therefore of a compound or salt thereof according to claim 1.

* * * * *